(12) United States Patent
Speitling et al.

(10) Patent No.: US 7,923,003 B2
(45) Date of Patent: Apr. 12, 2011

(54) ADHESIVE FOR MEDICAL APPLICATIONS AND MEANS FOR HAEMOSTASIS

(75) Inventors: Andreas Werner Speitling, Kiel (DE); Philip Procter, Divonne-les-Bains (FR); Joachim Schomburg, Neubrandenburg (DE); Christian Schultz, Neubrandenburg (DE); Wolf Dieter Jülich, Greifswald (DE); Ulrike Lindequist, Greifswald (DE); Frieder Schauer, Lubmin (DE); Annett Mikolasch, Greifswald (DE); Katrin Manda, Putbus (DE)

(73) Assignee: Stryker Trauma GmbH (DE)

( * ) Notice: Subject to any disclaimer, the term of this patent is extended or adjusted under 35 U.S.C. 154(b) by 0 days.

(21) Appl. No.: 12/223,772

(22) PCT Filed: Feb. 9, 2007

(86) PCT No.: PCT/EP2007/001131
§ 371 (c)(1),
(2), (4) Date: Dec. 22, 2008

(87) PCT Pub. No.: WO2007/090673
PCT Pub. Date: Aug. 16, 2007

(65) Prior Publication Data
US 2009/0318584 A1    Dec. 24, 2009

(30) Foreign Application Priority Data
Feb. 9, 2006 (DE) .......................... 10 2006 006 904

(51) Int. Cl.
A61K 31/74 (2006.01)
A01N 1/00 (2006.01)
C09J 189/00 (2006.01)
A61F 15/00 (2006.01)

(52) U.S. Cl. ............ 424/78.06; 514/2; 523/111; 602/48

(58) Field of Classification Search .................. 525/192; 602/48; 523/111; 424/78.06; 514/2
See application file for complete search history.

(56) References Cited

U.S. PATENT DOCUMENTS

| | | | | |
|---|---|---|---|---|
| 4,487,810 A | * | 12/1984 | Ascarelli et al. | 428/461 |
| 4,542,115 A | * | 9/1985 | Strack et al. | 502/64 |
| 5,015,677 A | * | 5/1991 | Benedict et al. | 524/17 |
| 5,494,744 A | * | 2/1996 | Everhart et al. | 428/337 |
| 6,884,230 B1 | * | 4/2005 | Epstein et al. | 604/82 |
| 2003/0187387 A1 | | 10/2003 | Wirt et al. | |
| 2004/0037906 A1 | * | 2/2004 | Li et al. | 424/757 |
| 2005/0002893 A1 | * | 1/2005 | Goldmann | 424/70.27 |
| 2005/0074505 A1 | * | 4/2005 | Hursey | 424/682 |
| 2006/0025560 A1 | * | 2/2006 | Inoue et al. | 528/272 |

FOREIGN PATENT DOCUMENTS

| | | |
|---|---|---|
| EP | 947 142 | 10/1999 |
| WO | WO-00/69480 A | 11/2000 |
| WO | WO-03/035122 A | 5/2003 |

OTHER PUBLICATIONS

SU 1725786 A1 Derwent Abstract, Geodakyan, R. O. et al. Apr. 15, 1992.*
RU 2131198 C1 Derwent Abstract, Tsaregorodtseva, G. N. Jun. 10, 1999.*
KR 98059063 A Derwent Abstract, Chung, G. H. et al. Oct. 7, 1998.*
JP 04266764 A Derwent Abstract, Koide M. Sep. 22, 1992.*
Derwent abstract of SU Patent Pub No. 1725786 A1, Geodakyan et al., Apr. 15, 1992.*
Derwent abstract of RU Patent Pub No. 2131198 C1, Tsaregorodtseva, G. N., Jun. 10, 1999.*
Derwent abstract of KR Patent Pub No. 98059063 A, Chung et al., Oct. 7, 1998.*
Derwent abstract of JP Patent Pub No. 04266764 A, Koide, M., Sep. 22, 1992.*
Von Friedrich Burkhardt, Mikrobiologische Diagnostik, p. 724, 1992 Georg Thieme Verlag Stuttgart, New York.
Alam, et al., "Comparative Analysis of Hemostatic Agents in a Swine Model of Lethal Groin Injury", The Journal of Trauma Injury, Infection and Critical Care, vol. 54, No. 6, pp. 1077-1082.
Schroder, et al., "Improvement of Low-pressure Microwave Plasma-assisted Amino Functionalization of Polymers," Plasma Life and Science, 2005, pp. 333-349.
Schroder, et al., "Plasma-Induced Surface Functionalization of Polymeric Biomaterials in Ammonia Plasma," Contrib. Plasma Phys. 41, Oct. 3, 2001, pp. 562-572.
Meyer-Plath, et al., "Current Trends in Biomaterial Surface Functionalization Nitrogen-Containing Plasma Assisted Procsses with Enhanced Selectivity," Science Direct, Vacumm 71 (2003), pp. 391-406.
Von Friedrich Burkhardt, Mikrobiologische Diagnostik, p. 724, 1992 Georg Thieme Verlag Stuttgart, New York.

* cited by examiner

*Primary Examiner* — Mark Eashoo
*Assistant Examiner* — David Karst
(74) *Attorney, Agent, or Firm* — Lerner, David, Littenberg, Krumholz & Mentlik, LLP

(57) ABSTRACT

The invention relates to a kit comprising the following individual components: (a) polymers comprising at least one free amino group, (b) bridge molecules selected from the group consisting of monocyclic ortho-dihydroxyaromates, monocyclic para-dihydroxyaromates, bicyclic monohydrxyaromates, polycyclic monohydroxyaromates, bicyclic dihydroxyaromates, polycyclic dihydroxyaromates, bicyclic trihydroxyaromates, polycyclic trihydroxyaromates, and mixtures thereof, and (c) polyphenoloxidases, in particular, lignolytic polyphenoloxidases, whereby the individual components b) and c) are not in contact.

27 Claims, No Drawings

ADHESIVE FOR MEDICAL APPLICATIONS AND MEANS FOR HAEMOSTASIS

The invention relates to adhesives for medical applications and means for haemostasis. In particular, the invention relates to a kit for the manufacture of an adhesive suitable for adhering hard and soft tissue to each other, for the closure of wounds, as well as the adhesive itself and its uses in the medical field. The kit and the corresponding adhesive comprise, as individual components, substrates of the polyphenoloxidase as well as polyphenoloxidases as such. Furthermore, the invention relates to novel haemostatics as well as the combined use of haemostatics and adhesives in the closure of wounds.

PRIOR ART

The development of novel adhesives for tissue that can be applied, especially in problematic cases, has strongly gained importance in the past few years. Adhesives for tissue on the basis of acrylate used so far can only be applied to superficial wounds, since acrylates are not decomposed biologically and could impose a toxic hazard. One focus is, therefore, on the biological decomposability of the used materials. Therefore, polymers of vegetable or animal origin are of special importance in the manufacture of adhesives. Mussels can have strong bonds with various carrier substrates under water. The reason for this is the formation/excretion of MAPs (mussel adhesive proteins). MAPs consist of a number of proteins that can vary depending on the type of mussel. In U.S. Pat. No. 5,015,677 A, a mussel adhesive is protected containing as an essential component a very special decapeptide isolated from mussels. This decapeptide contains dehydroxyaromates as substituents of very special amino acids that form an essential component of the peptide chain. The peptide chains are then bonded with each other by means of a tyrosinase. Further satisfying solutions that make it possible to bond bones with implants by means of an adhesive are not known.

EP 0 947 142 discloses increasing the molecular weight of proteins by crosslinking by means of multi-copper enzymes. The described increasing of the molecular weight of the substrate proteins occurred seventeen hours after incubation. The proteins crosslinked using the method of EP 0 947 142 are especially suitable for the use in food, for example for modifying the consistence of sausage. Crosslinking of proteins by means of substituted dihydroxyaromates is not disclosed in EP 0 947 142.

If adhesives for wounds are intended to be used in case of strongly bleeding wounds, there is the danger that adhesive components are washed away with the bloodstream and the adhesion occurs at a site where it is not desired. Thus, the danger of thrombosis is strongly increased. Acute treatment of strongly bleeding wounds is still a problem that is not solved satisfyingly. Haemostasis according to the state of the art can be achieved by (a) Denaturation of proteins, for example by means of metal salts
(b) Microporous biopolymers or biopolymers having a great inner surface, respectively. They resorb water, and, therefore, cause concentration of blood cells as well as coagulation factors. Polysaccharides consisting of poly-N-acetyl-glucosamines or chitosan have proved to be especially advantageous. They are, for example, contained in the skeleton of insects, but also in algae. Biopolymers such as gelatin, collagen, fibrin sponges or oxidized cellulose have a great inner surface. A concentration of coagulation factors is caused by absorption onto these great surfaces.
(c) Enzymes, especially by thrombin or proteolytic enzymes having thrombin-like activity with or without the addition of calcium.
(d) Highly concentrated coagulation factors
(e) Combinations of (c) and (d)
(f) Calcium alginates
(g) Alumosilicate synthesis products having a microporous structure.

Alumosilicate synthesis products used for haemostasis are alkaline or alkaline-earth alumosilicates of differing composition.

The company Z-Medica, U.S. has developed a synthesis product on the basis of synthesized earth-alkali alumosilicates that completely dehydrate at above 400° C. for the immediate treatment of war injuries and for emergency use. Because of the strongly exothermic reaction, blood is dehydrated causing haemostasis. The synthesis product is directly applied to the wound as a granulate. It is marketed under the designation "Quikclot." A disadvantage has been described for this product in that because of the exothermic reaction (temperatures up to 60° C.) adjacent tissue can be damaged (Journal of Trauma 54 (2003) 6, 1077-1082).

Synthetic lithium alumosilicates (EP 1 176 991 A1, WO 00/69480) were developed especially for the treatment of wounds and are marketed under the designation CERDAC. In the case of CERDAC, a microporous ceramic product is produced using high temperatures (>1000° C.) in order to obtain optimal treatment of wounds.

The capillary force action is too low, apart from the partly complicated production, to satisfy all requirements.

A great problem is still the possible chronification of wounds, especially in case of risk patients. This so far cannot be avoided for certain, and the treatment of such wounds is still very difficult. Chronification often involves an infection of the wound.

Four million patients suffer from chronically open wounds in Germany alone. The annual costs amount to €1.7 to €3.2 billion. The treatment of chronic wounds so far has not been solved satisfyingly.

It can be summarized that for the problem of adhering hard and soft tissue as well: as for the rapid closure, the treatment of strongly bleeding and especially the treatment of chronic wounds, no completely satisfying solutions have been achieved yet.

The present object is to solve the problem described in the prior art by means of products having efficient adhesive properties for hard and soft tissue. In particular, systems such as adhesives should be provided, enabling stopping the bleeding of strongly bleeding wounds and/or strongly adhering bone parts with each other or bone parts with implants. Further desired are adhesives enabling soft tissue with bones, such as cartilage transplants. The inventive possibilities for the closure of wounds should preferably be usable for chronic and infected wounds.

The finding of the present invention is that polymers that have at least one free amino group are crosslinked by means of bridge molecules using (lignolytic) polyphenoloxidases to provide covalent linkages with each other and/or with body tissue so that they can be used as an adhesive for hard and soft tissue.

A further finding of the present invention is that specifically processed natural zeolites cause a rapid stopping of bleeding.

In this respect, the present invention relates in a first embodiment to a kit, comprising the following individual components:
(a) Polymers having at least one free amino group,
(b) Bridge molecules, selected from the group consisting of monocyclic ortho-dihydroxyaromates, monocyclic para-dihydroxyaromates, bicyclic monohydroxyaromates, polycyclic monohydroxyaromates, bicyclic dihydroxyaromates, polycyclic dihydroxyaromates, bicyclic trihydroxyaromates, polycyclic trihydroxyaromates, and mixtures thereof, and
(c) Polyphenoloxidases, in particular lignolytic polyphenoloxidases,
wherein both individual components (components (b) and (c)), i.e. the bridge molecules polyphenoloxidases, in particular lignolytic polyphenoloxidases, are not in contact.

In the context of the present invention, a kit is particularly a package providing for the storage of the individual components next to each other, so that they are not in contact. In the present case, at least the bridge molecules (component (b)) need to be separated from the (lignolytic) polyphenoloxidases (component (c)), in order to avoid a premature and undesired reaction. Thus, a mixture of components (a) and (b) and/or components (a) and (c) is possible.

Both individual components may preferably be stored in different containers or chambers, in order to avoid contact between the bridge molecules and the (lignolytic) polyphenoloxidases. This is also true in case that one or both individual components (b) and (c) are mixed with the polymer (a). A syringe may be considered enabling the administration of both individual components, i.e. the bridge molecules and the (lignolytic) polyphenoloxidases, separate from each other by means of two cannulae. Here it is preferred that both individual components, i.e. the bridge molecules and the (lignolytic) polyphenoloxidases, are present in the syringe in different chambers. Of course, it may also be considered that the kit comprises two syringes wherein one contains the bridge molecules and the other the (lignolytic) polyphenoloxidases.

In one embodiment, the kit is a double-chambered syringe, preferyble already having a mixing extruder added. This provides for an especially exact dosing and ease of handling. A double-chambered syringe of the Mixpac type (Mixpac Systems AG, Rotkreuz, Switzerland) is, for example, preferred.

It is to be understood that in the context of the invention, one or more different, individual components (a), (b), and (c) may independently be used. Singular and plural is, therefore, used for all components synonymously.

It is an essential requirement that the kit comprises polymers (a) having at least one free amino group as an individual component. In the present invention, a free amino group means an amino group that is not part of the polymer chain, but is a radical of the polymer chain. These polymers are not part of the human body, since they are present in the kit. The polymers are preferably polymers having more than one amino group, i.e. polymers rich in amino groups, such as peptides.

Peptides (i.e. oligopeptides and proteins) naturally have an amide bond between the amino acids. The peptides preferably contain lysine. In a preferred embodiment of the invention, lysine-containing oligopeptides are used. Collagen may be considered as the peptide.

If the polymer is a peptide, there is a special advantage in that the compound obtained by reaction of the component is biologically decomposable. By linking peptide sequences containing the amino acids relevant for the adhesive action, a very strong adhesion is formed that can, however, be resorbed during the process of healing. The initial hardening phase involving highly adhesive properties, and the time-depending slow absorption into the body during advanced healing processes are especially advantageous, since body tissue is increasingly fixed into the adhesion site.

In the present invention, an oligopeptide (2 to about 100 amino acids long, preferably about 4 to about 20 amino acids long, or about 6 to about 10 amino acids long) as well as a protein (about 100 to about 5,000 amino acids long, preferably 100-1,000 or 100-200 amino acids long) is considered a peptide. The peptide is preferably 10-1,000 amino acids long. The peptide can have a molecular weight of about 1 to about 100 or to about 200 kDa, in particular about 2 to about 50 kDa, or about 5 to about 20 kDa. It can be modified or substituted, e.g. can be glycosylized. Apart from conventional proteinogenic amino acids, modified or atypical amino acids such as hydroxylysine may be contained in the oligopeptide. The use of D-amino acids in place of or in addition to L-amino acids is possible and retards decomposition of the peptide.

The amino groups may preferably be primary or secondary amino groups. However, primary amino groups are especially reactive. At least one of the reactive groups of the peptide is part of a diamino acid, e.g. lysine. Therefore, the peptide preferably comprises at least one diamino acid, preferably at least 2, 3, 4, 5 or more diamino acids. As mentioned above, lysine-containing peptides (oligopeptides or proteins) are preferably used.

Other amino acids, such as arginine, asparagine, glutamine, or histidine also have reactive amino groups that may react with the dihydroxyaromates.

The amino groups, especially the amino groups provided by the diamino acid, are especially suitable for the crosslinking reaction between the peptide and the bridge molecule. However, hydroxyl groups and mercapto groups in the peptide may also contribute to the crosslinking reaction. Therefore, the peptide preferably comprises at least one amino acid having a hydroxyl group, which means especially serine, threonine, or tyrosine, or a mercapto group, e.g. cysteine. Hydroxylysine or polyphenolic amino acid components, of the type present in MAPs, may be present in the peptides used according to the invention. An advantage of the invention is, however, that the presence of these specific amino acid components and, therefore, the use of MAPs is not mandatory. Therefore, in a preferred embodiment, the polymer is free of polyphenolic amino acid components, i.e. is free of MAPs. The used peptides may easily be prepared using recombination.

The crosslinking obtained by reaction of the bridge molecules with a peptide also depends on the proportion of the available reactive groups in the peptide. Good adhesive properties may be obtained with an amount of amino acids of the peptide having a reactive amino group (e.g. diamino acids such as lysine) of at least 10%. If the polymer is not a peptide the amount of structural elements of the polymer having an amino group is preferably at least 10%. However, the amount of these amino acids or structural elements is more preferably higher, at least 20%, at least 30%, at least 40%, or at least 50%, or even at least 80% to 100%. Naturally occurring peptides and proteins, e.g. albumine or caseine, may be used, MAPs are especially suitable.

However, shorter peptides that can easily be prepared synthetically may further also be used. In an especially preferred embodiment of the invention, at least 50% of the amino acids of the peptide is lysine. Lysine and a further amino acid may, for example, by arranged as a repeating dipeptide unit. However, a different sequence or the incorporation of further amino acids, in particular of arginine, asparagine, glutamine, or histidine (in place of or in addition to lysine), serine, or threonine (in place of or in addition to tyrosine), of cysteine or other amino acids is possible. The peptide lengths of about 10-20 amino acids or a mixture of peptides having different chain lengths is especially preferred.

In a preferred embodiment, the polymers consist exclusively of two amino acids, for example (lysine-thyrosine)$_n$, wherein n can have values between 5 and 40, such as 5, 10, or 20.

A further essential requirement of the present invention is that the kit comprises bridge molecules causing a crosslinking of polymers that have at least one free amino group (such as diamino acids).

Generally, substituted dihydroxyaromates and/or substrates of the (lignolytic) polyphenoloxidases, such as laccases, are suitable as bridge molecules.

Thus, monocyclic ortho-dihydroxyaromates, monocyclic para-dihydroxyaromates, bicyclic monohydroxyaromates, polycyclic monohydroxyaromates, bicyclic dihydroxyaromates, polycyclic dihydroxyaromates, bicyclic trihydroxyaromates, polycyclic trihydroxyaromates, or mixtures thereof are used. The hydroxyaromates according to the invention are not part of the polymer chain, as opposed to the known mussel adhesives.

It may be considered that these aromates are further substituted. Preferred functional groups are substituents selected from the group consisting of halogen, sulfo-, sulfon-, sulfamido, sulfanyl-, amino-, amido-, azo-, immino-, and hydroxyl. Here it can especially be found that substituted aromates, in particular substituted dihydroxyaromates have surprisingly advantageous polymerization properties, in particular a rapid polymerization, a low self-coupling, and a good steadiness of the adhesion is obtained. Suitable substitution of the aromates may cause that even monohydroxyaromates as bridge molecules are suitable for crosslinking. Substituted in the context of this invention means, in particular, that 1, 2, 3, or 4 further radicals are bonded to the aromates apart from the hydroxyl groups. On the other hand, monohydroxylated biaryl compounds are also suitable.

Phenol derivatives having a hydroxyl group or a methoxy group in ortho- or para position are especially preferred. Thus, the following compounds of formulae 3 and 4 are preferred:

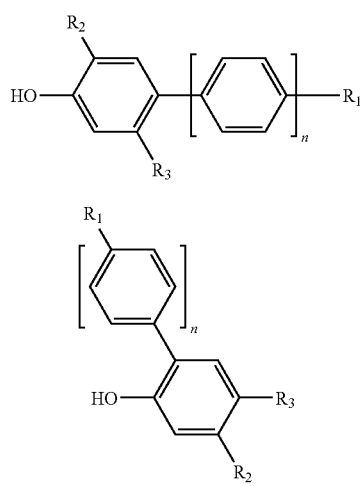

wherein
n=0-10, preferably 0 or 1, especially 0,
R$_1$=OH or NH$_2$ or Hal, preferably OH, Cl, or Br, especially OH,
R$_2$=H, CH$_3$, CHO, COCH$_3$, CONH$_2$, CON-alkyl, CON-alkyl-OH, COOH, COO-alkyl, alkyl, substituted aromate, especially CON-alkyl or COO-alkyl, and
R$_3$=H, CH$_3$, alkyl, substituted aromate, especially H or CH$_3$.

Alkyl means branched or non-branched aliphatic hydrocarbon chains, preferably having 1-20, more preferably 1-6 carbon atoms, e.g. methyl, ethyl, propyl, butyl, isobutyl, n-pentyl, n-hexyl.

Compounds of formula 3 and the hydrochinone thereof, which may be further substituted, are possible. In view of a rapid adhesive reaction, substituted dihydroxyaromates having a low self-coupling are especially suitable according to the invention. 2,5-dihydroxybenzamide is preferably used, 2,5-dihydroxy-N-(2-hydroxyethyl)-benzamide is especially preferred.

In the case of trihydroxyaromates, it is preferred that not more than two hydroxy groups are present per benzene unit. Especially preferred are polyphenyls, i.e. biphenyl or triphenyl of the following formula 5:

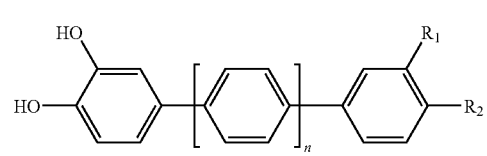

wherein
n=0-10, preferably 0 or 1 and
R$_1$=H and R$_2$=OH or R$_1$=OH and R$_2$=H.

The phenyls of formula 5 may be substituted, e.g. in ortho position of the OH group with CH$_3$, CHO, COCH$_3$, CONH$_2$, CON-alkyl, CON-alkyl-OH, COOH, COO-alkyl, alkyl, substituted aromate, especially CON-alkyl or COO-alkyl, and/or in meta position of the OH group with CH$_3$, alkyl, substituted aromate, especially CH$_3$.

It is further required that the kit comprises polyphenoloxidases as a further individual component, such as lignolytic polyphenoloxidases, especially laccases (EC 1.10.3.2). Laccases are known in the art. They may be of plant, fungi, bacteria, or insect origin, or be derived from natural enzymes. Laccases used according to the invention may be prepared or purified using recombination. Generally, special purity of the laccase is not required, fluids of lignolytic fingi may optionally be used. However, for medical applications, substantial removal of microbiological substances, such as lipopolysaccharides or other components of the cell wall, is often desirable.

Examples are laccase of the genus *Aspergillus, Neurospora, Podospora, Botrytis, Collybia, Fomes, Lentinus, Pleurotus, Pycnoporus, Pyricularia, Trametes, Rhizoctonia, Coprinus, Psatyrella, Myceliophthora, Schtalidium, Polyporus, Phlebia,* or *Coriolus*. The manufacture of laccases is disclosed, for example, in EP 0 947 142.

By the use of polyphenoloxidases, such as lignolytic polyphenoloxidases, preferably laccase (EC 1.10.3.2) in the kit, their broad as well as special substrate spectrum can be used for the adhesive reaction. Therefore, the kit is especially characterized in that the adhesive reaction is not limited to special natural peptides acting as bridge molecules, but a broad spectrum of bridge molecules, on the one hand, and of peptides such as oligopeptides or proteins, on the other hand, may be used.

Variations of the amounts of the individual component (a), in particular of the peptide, as well as of the bridge molecule, are possible in the range of about 1-50 mM. For each application the optimal ratio of the amounts is to be determined using preliminary tests.

It has to be considered that depending on the selected bridge molecule, a reaction of the bridge molecule with itself takes place decreasing the formation of crosslinking products. Too low a concentration of the bridge molecules leads to a slow reaction, too high a concentration to increased byreactions due to self-coupling. When a lower ratio of peptides is present, reactive amino-, mercapto and/or hydroxyl groups of the substrates to be adhered are increasingly included in the crosslinking. The amount of polyphenoloxidase has an influence on the reaction rate wherein the rapid reach of the gel point or the complete hardening or prolonged processability of the combination can be obtained depending on the application. The kit can be adjusted to the respective concrete problem by optimizing the ratio of amounts in preliminary tests.

It is a special advantage of the kit that the components in the kit are present in an optimized ratio of amounts appropriate for the intended use. A preferred ratio of amounts for adhering soft tissue is, for example, $[\text{Tyr-Lys}]_{n,\ n=4-35}$, 8.5 mM; 2,5-dihydroxy-N-(2-hydroxyethyl)-benzamide 12.5 mM; polyphenoloxidase: 32 U (156 nmol ml$^{-1}$ min$^{-1}$). The ratio of amounts may be selected in advance in the kit and prevents complicated individual dosing of the ingredients.

The combination used in the kit can contain further additives and adjuvants, e.g. fillers, such as collagen, albumine, hyaluronic acid or the like. The total proportion of individual component (a), such as peptide, and bridge molecule is preferably about 50%-90%.

The essential components of the kit are preferably dissolved in one or more aqueous solvents. For medical applications, the solvent is non-toxic and biologically acceptable. A phosphate buffer, such as calcium phosphate or sodium phosphate buffer or PBS, is preferred as a solvent for biological applications. For other applications, an organic solvent, such as DMSO, or a mixture of an aqueous and an organic solvent, may be used. Alternatively, the combination or its components may be dissolved in the solvent and introduced into the kit only prior to use.

The consistency of the components used in the kit does not, however, need to be liquid, but may have a paste-like consistency. The viscosity and flowability of the used individual components may be adjusted, depending on e.g. the length of the wound to be fixed and the depth of the wound gap or the substrates to be adhered, respectively. Apart from the length of the used peptides/polymers, the amount of solvent also has an influence on these parameters. Additives, such as thixotropic agents, may be used for adjusting viscosity and flowability. Typically, a combination of higher viscosity is used for adhering hard tissue than for adhering soft tissue.

The pH is preferably 2-10, especially 5-7. The reaction can proceed at 2-80° C.; however, the temperature is preferably about 20-37° C. or 25-30° C. Thus, the adhesive reaction of the kit can be carried out at room temperature/body temperature.

There are no special requirements for storage, unlike in the case of frozen fibrin adhesives. The (lignolytic) polyphenoloxidase, such as laccase, may be used in dissolved form, wherein storage at temperatures of a refrigerator is sufficient. It is also possible to provide the lignolytic polyphenoloxidase, such as laccase, in the form of a powder and to dissolve it in advance of an intended application.

Sterilization of the kit or its individual components may preferably be achieved without structural changes. For example, a solution may be sterilized using filtration. However, sterilization by means of gamma radiation is preferred, since this can be carried out after packaging, so that packaging under aseptic conditions is unnecessary. The loss of activity of the (lignolytic) polyphenoloxidase, such as laccase, due to gamma sterilization which can amount to up to 50% may be compensated using a correspondingly higher initial concentration.

The above-defined kit is preferably used as a medicament. Classification as a pharmaceutical preparation or a medical preparation is also possible depending on national law. These terms can be interchanged in the context of the invention.

In a further aspect, the present invention relates to an adhesive having the individual components described above.

Thus, the adhesive comprises the following individual components:
(a) Polymers having at least one free amino group, wherein the polymers are not part of the human body,
(b) Bridge molecules, selected from the group consisting of monocyclic ortho-dihydroxyaromates, monocyclic para-dihydroxyaromates, bicyclic monohydroxyaromates, polycyclic monohydroxyaromates, bicyclic dihydroxyaromates, polycyclic dihydroxyaromates, bicyclic trihydroxyaromates, polycyclic trihydroxyaromates, and mixtures thereof, and
(c) Polyphenoloxidases, especially lignolytic polyphenoloxidases,
wherein both individual components (components (b) and (c)), i.e. the bridge molecules with the polyphenoloxidases, especially the lignolytic polyphenoloxidases, are not in contact, i.e. mixed with each other.

As regards the individual components, it is referred to the description of the kit.

It is, therefore, to be understood that, according to the invention, one or more different individual components (a), (b), and (c) may be used independently of each other. Singular and plural is, therefore, used synonymously with regard to all components.

It is an essential requirement that the adhesive comprises polymers (a) having at least one free amino group as an individual component. In the present invention, a free amino group means an amino group that is not part of the polymer chain, but is a radical of the polymer chain. These polymers are not part of the human body, since they are present in the adhesive. The polymers are preferably polymers having more than one amino group, i.e. polymers rich in amino groups, such as peptides.

Peptides (i.e. oligopeptides and proteins) naturally have an amide bond between the amino acids. The peptides preferably contain lysine. In a preferred embodiment of the invention, lysine-containing oligopeptides are used. Collagen may be considered as the peptide.

If the polymer is a peptide, there is a special advantage in that the compound obtained by reaction of the component is biologically decomposable. By linking peptide sequences containing the amino acids relevant for the adhesive action, a very strong adhesion is formed that can, however, be resorbed during the process of healing. The initial hardening phase involving highly adhesive properties, and the time-depending slow absorption into the body during advanced healing processes are especially advantageous, since body tissue is increasingly fixed into the adhesion site.

In the present invention, an oligopeptide (2 to about 100 amino acids long, preferably about 4 to about 20 amino acids long, or about 6 to about 10 amino acids long) as well as a protein (about 100 to about 5,000 amino acids long, preferably 100-1,000 or 100-200 amino acids long) is considered a peptide. The peptide is preferably 10-1,000 amino acids long.

The peptide can have a molecular weight of about 1 to about 100 or to about 200 kDa, in particular about 2 to about 50 kDa, or about 5 to about 20 kDa. It can be modified or substituted, e.g. can be glycosylized. Apart from conventional proteinogenic amino acids, modified or atypical amino acids such as hydroxylysine may be contained in the oligopeptide. The use of D-amino acids in place of or in addition to L-amino acids is possible and retards decomposition of the peptide.

The amino groups may preferably be primary or secondary amino groups. However, primary amino groups are especially reactive. At least one of the reactive groups of the peptide is part of a diamino acid, e.g. lysine. Therefore, the peptide preferably comprises at least one diamino acid, preferably at least 2, 3, 4, 5 or more diamino acids. As mentioned above, lysine-containing peptides (oligopeptides or proteins) are preferably used.

Other amino acids, such as arginine, asparagine, glutamine, or histidine also have reactive amino groups that may react with the dihydroxyaromates.

The amino groups, especially the amino groups provided by the diamino acid, are especially suitable for the crosslinking reaction between the peptide and the bridge molecule. However, hydroxyl groups and mercapto groups in the peptide may also contribute to the crosslinking reaction. Therefore, the peptide preferably comprises at least one amino acid having a hydroxyl group, which means especially serine, threonine, or tyrosine, or a mercapto group, e.g. cysteine. Hydroxylysine or polyphenolic amino acid components, of the type present in MAPs, may be present in the peptides used according to the invention. An advantage of the invention is, however, that the presence of these specific amino acid components and, therefore, the use of MAPs is not essentially required. Therefore, in a preferred embodiment, the polymer is free of polyphenolic amino acid components, i.e. is free of MAPs. The used peptides may easily be prepared using recombination.

The crosslinking obtained by reaction of the bridge molecules with a peptide also depends on the proportion of the available reactive groups in the peptide. Good adhesive properties may be obtained with an amount of amino acids of the peptide having a reactive amino group (e.g. diamino acids such as lysine) of at least 10%. If the polymer is not a peptide the amount of structural elements of the polymer having an amino group is preferably at least 10%. However, the amount of these amino acids or structural elements is more preferably higher, at least 20%, at least 30%, at least 40%, or at least 50%, or even at least 80% to 100%. Naturally occurring peptides and proteins, e.g. albumine or caseine, may be used, MAPs are especially suitable.

However, shorter peptides that can easily be prepared synthetically may further also be used. In an especially preferred embodiment of the invention, at least 50% of the amino acids of the peptide is lysine. Lysine and a further amino a-lid may, for example, by arranged as a repeating dipeptide unit. However, a different sequence or the incorporation of further amino acids, in particular of arginine, asparagine, glutamine, or histidine (in place of or in addition to lysine), serine, or threonine (in place of or in addition to tyrosine), of cysteine or other amino acids is possible. The peptide lengths of about 10-20 amino acids or a mixture of peptides having different chain lengths is especially preferred.

In a preferred embodiment, the polymers consist exclusively of two amino acids, for example (lysine-thyrosine)$_n$, wherein n can have values between 5 and 40, such as 5, 10, or 20.

A further essential requirement of the present invention is that the adhesive comprises bridge molecules causing a crosslinking of polymers that have at least one free amino group (such as diamino acids), as defined above.

Generally, substituted dihydroxyaromates and/or substrates of the (lignolytic) polyphenoloxidases, such as laccases, are suitable as bridge molecules.

Thus, monocyclic ortho-dihydroxyaromates, monocyclic para-dihydroxyaromates, bicyclic monohydroxyaromates, polycyclic monohydroxyaromates, bicyclic dihydroxyaromates, polycyclic dihydroxyaromates, bicyclic trihydroxyaromates, polycyclic trihydroxyaromates, or mixtures thereof are used. The hydroxyaromates according to the invention are not part of the polymer chain, as opposed to the known mussel adhesives.

It may be considered that these aromates are further substituted. Preferred functional groups are substituents selected from the group consisting of halogen, sulfo-, sulfon-, sulfamido, sulfanyl-, amino-, amido-, azo-, immino-, and hydroxyl. Here it can especially be found that substituted aromates, in particular substituted dihydroxyaromates have surprisingly advantageous polymerization properties, in particular a rapid polymerization, a low self-coupling, and a good steadiness of the adhesion is obtained. Suitable substitution of the aromates may cause that even monohydroxyaromates as bridge molecules are suitable for crosslinking. Substituted in the context of this invention means, in particular, that 1, 2, 3, or 4 further radicals are bonded to the aromates apart from the hydroxyl groups. On the other hand, monohydroxylated biaryl compounds are also suitable.

Phenol derivatives having a hydroxyl group or a methoxy group in ortho- or para position are especially preferred. Thus, the following compounds of formulae 3 and 4 are preferred:

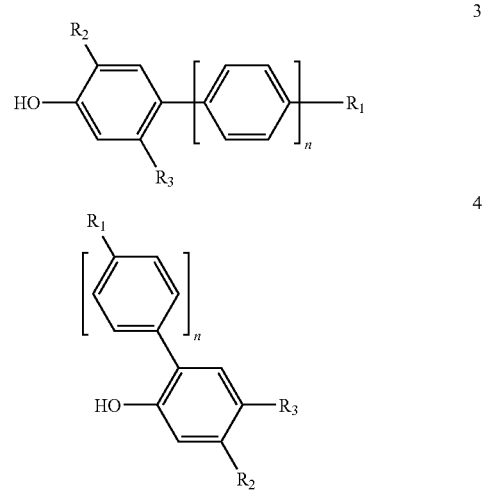

wherein
n=0-10, preferably 0 or 1, especially 0,
$R_1$=OH or $NH_2$ or Hal, preferably OH, Cl, or Br, especially OH,
$R_2$=H, $CH_3$, CHO, $COCH_3$, $CONH_2$, CON-alkyl, CON-alkyl-OH, COOH, COO-alkyl, alkyl, substituted aromate, especially CON-alkyl or COO-alkyl, and
$R_3$=H, $CH_3$, alkyl, substituted aromate, especially H or $CH_3$.

Alkyl means branched or non-branched aliphatic hydrocarbon chains, preferably having 1-20, more preferably 1-6 carbon atoms, e.g. methyl, ethyl, propyl, butyl, isobutyl, n-pentyl, n-hexyl.

Compounds of formula 3 and the hydrochinone thereof, which may be further substituted, are possible. In view of a rapid adhesive reaction, substituted dihydroxyaromates having a low self-coupling are especially suitable according to the invention. 2,5-dihydroxybenzamide is preferably used, 2,5-dihydroxy-N-(2-hydroxyethyl)-benzamide is especially preferred.

In the case of trihydroxyaromates, it is preferred that not more than two hydroxy groups are present per benzene unit. Especially preferred are polyphenyls, i.e. biphenyl or triphenyl of the following formula 5:

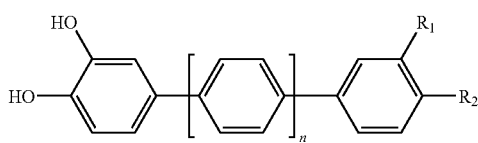

wherein
n=0-10, preferably 0 or 1 and
$R_1$=H and $R_2$=OH or $R_1$=OH and $R_2$=H.

The phenyls of formula 5 may be substituted, e.g. in ortho position of the OH group with $CH_3$, CHO, $COCH_3$, $CONH_2$, CON-alkyl, CON-alkyl-OH, COOH, COO-alkyl, alkyl, substituted aromate, especially CON-alkyl or COO-alkyl, and/or in meta position of the OH group with $CH_3$, alkyl, substituted aromate, especially $CH_3$.

It is further required that the adhesive comprises polyphenoloxidases as a further individual component, such as lignolytic polyphenoloxidases, especially laccases (EC 1.10.3.2). Laccases are known in the art. They may be of plant, fungi, bacteria, or insect origin, or be derived from natural enzymes. Laccases used according to the invention may be prepared or purified using recombination. Generally, special purity of the laccase is not required, fluids of lignolytic fingi may optionally be used. However, for medical applications, substantial removal of microbiological substances, such as lipopolysaccharides or other components of the cell wall, is often desirable. Examples are laccase of the genus *Aspergillus, Neurospora, Podospora, Botrytis, Collybia, Fomes, Lentinus, Pleurotus, Pycnoporus, Pyricularia, Trametes, Rhizoctonia, Coprinus, Psatyrella, Mycelioph-thora, Schtalidium, Polyporus, Phlebia,* or *Coriolus*. The manufacture of laccases is disclosed, for example, in EP 0 947 142.

By the use of polyphenoloxidases, such as lignolytic polyphenoloxidases, preferably laccase (EC 1.10.3.2) in the adhesive, their broad as well as special substrate spectrum can be used for the adhesive reaction. Therefore, the adhesive is especially characterized in that the adhesive reaction is not limited to special natural peptides acting as bridge molecules, but a broad spectrum of bridge molecules, on the one hand, and of peptides such as oligopeptides or proteins, on the other hand, may be used.

Variations of the amounts of the individual component (a), in particular of the peptide, as well as of the bridge molecule, are possible in the range of about 1-50 mM. For each application the optimal ratio of the amounts is to be determined using preliminary tests.

It has to be considered that depending on the selected bridge molecule, a reaction of the bridge molecule with itself takes place decreasing the formation of crosslinking products. Too low a concentration of the bridge molecules leads to a slow reaction, too high a concentration to increased byreactions due to self-coupling. When a lower ratio of peptides is present, reactive amino-, mercapto and/or hydroxyl groups of the substrates to be adhered are increasingly included in the crosslinking. The amount of polyphenoloxidase has an influence on the reaction rate wherein the rapid reach of the gel point or the complete hardening or prolonged processability of the combination can be obtained depending on the application. The adhesive can be adjusted to the respective concrete problem by optimizing the ratio of amounts in preliminary tests.

It is a special advantage of the adhesive that the components in the adhesive are present in an optimized ratio of amounts appropriate for the intended use. A preferred ratio of amounts for adhering soft tissue is, for example, [Tyr-Lys]$_n$, $_{n=4-35}$, 8.5 mM; 2,5-dihydroxy-N-2-hydroxyethyl)-benzamide 12.5 mM; polyphenoloxidase: 32 U (156 nmol ml$^{-1}$ min$^{-1}$). The ratio of amounts may be selected in advance in the adhesive and prevents complicated individual dosing of the ingredients.

The combination used in the adhesive can contain further additives and adjuvants, e.g. fillers, such as collagen, albumine, hyaluronic acid or the like. The total proportion of individual component (a), such as peptide, and bridge molecule is preferably about 50%-90%.

The essential components of the adhesive are preferably dissolved in one or more aqueous solvents. For medical applications, the solvent is non-toxic and biologically acceptable. A phosphate buffer, such as calcium phosphate or sodium phosphate buffer or PBS, is preferred as a solvent for biological applications. For other applications, an organic solvent, such as DMSO, or a mixture of an aqueous and an organic solvent, may be used. Alternatively, the combination or its components may be dissolved in the solvent and introduced into the adhesive only prior to use.

The consistency of the components used in the adhesive does not, however, need to be liquid, but may have a paste-like consistency. The viscosity and flowability of the used individual components may be adjusted, depending on e.g. the length of the wound to be fixed and the depth of the wound gap or the substrates to be adhered, respectively. Apart from the length of the used peptides/polymers, the amount of solvent also has an influence on these parameters. Additives, such as thixotropic agents, may be used for adjusting viscosity and flowability. Typically, a combination of higher viscosity is used for adhering hard tissue than for adhering soft tissue.

The pH is preferably 2-10, especially 5-7. The reaction can proceed at 2-80° C.; however, the temperature is preferably about 20-37° C. or 25-30° C. Thus, the adhesive reaction of the adhesive can be carried out at room temperature/body temperature.

There are no special requirements for storage, unlike in the case of frozen fibrin adhesives. The (lignolytic) polyphenoloxidase, such as laccase, may be used in dissolved form, wherein storage at temperatures of a refrigerator is sufficient. It is also possible to provide the lignolytic polyphenoloxidase, such as laccase, in the form of a powder and to dissolve it in advance of an intended application.

Sterilization of the adhesive or its individual components may preferably be achieved without structural changes. For example, a solution may be sterilized using filtration. However, sterilization by means of gamma radiation is preferred, since this can be carried out after packaging, so that packaging under aseptic conditions is unnecessary. The loss of activity of the (lignolytic) polyphenoloxidase, such as laccase, due to gamma sterilization which can amount to up to 50% may be compensated using a correspondingly higher initial concentration.

The above-defined adhesive is preferably used as a medicament. Classification as a pharmaceutical preparation or a medical preparation is also possible depending on national law. These terms can be interchanged in the context of the invention.

In the following, uses of the inventive kits and adhesives are described in detail.

The finding of the present invention is that by means of bridge molecules using (lignolytic) polyphenoloxidases, such as laccase, crosslinking may be achieved providing covalent bonds with polymers that have at least one free amino group. Therefore, the present invention relates to the use of a kit or adhesive as defined above for the closure of wounds. It is, however, sufficient that the kit or adhesive comprises only the individual components (b) and (c) in order to cause the adhering of wounds or the like, as described further below. Thus, the present invention relates to the use of a kits comprising the following individual components:

(a) Bridge molecules, selected from the group consisting of monocyclic ortho-dihydroxyaromates, monocyclic para-dihydroxyaromates, bicyclic monohydroxyaromates, polycyclic monohydroxyaromates, bicyclic dihydroxyaromates, polycyclic dihydroxyaromates, bicyclic trihydroxyaromates, polycyclic trihydroxyaromates, and mixtures thereof, and (b) Polyphenoloxidases, in particular lignolytic polyphenoloxidases, wherein the individual components (components (a) and (b)), i.e. the bridge molecules with the polyphenoloxidases, especially lignolytic poylphenoloxidases, are not in contact, for the manufacture of an adhesive for adhering wounds, in particular of hard and soft tissue, as described in further detail below.

Thus, in the following, by kit or adhesive, a kit or adhesive is meant that comprises the two individual components "bridge molecules" and "polyphenoloxidases" or the three individual components "polymers having at least one free amipo group," "bridge molecules," and "polyphenoloxidases," wherein a kit or adhesive having the three individual components described here is preferred.

With respect to the individual components and their preferred embodiments, it is referred to the kit or adhesive defined above.

The kit and/or the adhesive can be used for adhering hard and soft tissue. For example, connective tissue, skin, tendon, organ, blood vessel, and/or nerve (soft tissue) and/or tooth and/or bone (hard tissue) can be adhered. Of course, different kinds of tissues can be adhered to each other, e.g. tendons and bones. A particularly preferred application is in adhering of wound edges or in adhering ruptures of various organs, such as liver, kidney, or spleen. Treatment of surgical wounds, e.g. after removal of tumors, is also possible with the inventive kit and/or adhesive. Further fields of application are in plastic, reconstructive, and/or cosmetic surgery, in particular for preventing the formation of scars induced during suturing of wounds.

Closure and sealing of liquid and air leakages, e.g. sealing of stitch channel bleeding in the surgery of vessels, in arterial bypass surgery or for sealing leakages of the lung in thoracic surgery.

An advantageous application of the kits and/or adhesives is the flexible, over a certain period of time resorbable sealing of anastomases and patches on vessels or hollow organs.

The kit and/or adhesive is also suitable for fixation of drug delivery devices and porous carrier structures or membranes for potential use in regenerative medicine (tissue engineering). Here it is of a special advantage that the adhesion can also be carried out with surfaces of non-biological origin, as long as they carry free amino groups. Free amino groups can also be obtained on such surfaces of non-biological origin according to methods known in the art, e.g. plasma methods (Schrbder et al., Improved low-pressure microwave plasma assisted amino functionalization of polymers, Plasma processes and polymers, Weinheim, Deutschland, Weinheim: Wiley-VCH, 2005; Schröder et al., Plasma-Induced Surface Functionalization of Polymeric Biomaterials in Ammonia Plasma, Contrib. Plasma Phys. 41, 2001, 562-572; Meyer-Plath et al., Current trends in biomaterial surface functionalization—nitrogen-containing plasma assisted processes with enhanced selectivity, Vacuum 71, 2003, 391-406).

The surfaces of e.g. implants or of drug delivery devices intended to be connected with adjacent tissue using the kit and/or adhesive should have a content of at least 2% free amino groups. The term "surface" refers not only to flat areas, but to boundary areas of a solid substrate in any form. Thus, substrates can also be beads or surfaces of complex shape.

Adhesion methods using the above-identified kits and/or adhesives usable in an aqueous environment are also an embodiment according to the invention that leads to a strong, crosslinked resorbable connection. This is due, in particular, to a strong connection caused by crosslinking via polymers carrying free amino acids and bridge molecules induced by (lignolytic) polyphenoloxidase, such as induced by laccase, as defined above.

The invention especially relates the method for adhering soft and hard tissue using a kit and/or adhesive as defined above. When adhering soft and hard tissue, the adhering of bones to bones may be concerned. Here small bone fragments that due to their size cannot be fixed at all or only unsatisfactorily using screws are fixed using the inventive kit and/or adhesive. Compared to metallic implants, a second surgery after healing of the fracture is unnecessary when using adhering by means of the inventive kit and/or adhesive. Furthermore, bones may be fixed to soft tissue using the inventive kit and/or adhesive. In particular, cartilage transplants (e.g. from tissue cultures), e.g. for treating arthritis, may be fixed sufficiently by means of the inventive kit and/or adhesive until growth onto a joint surface. Of particular advantage is the fact that the kit and/or adhesive is successively resorbed. Furthermore, implants can be fixed by means of the inventive kit and/or adhesive to bones. The adhesive force of screws is rather decreased, especially in osteoportic bones. The adhesive force of screws may be supported by adhering the outer surface of bones on a great area with the implant (e.g. a plate) by means of the inventive kits and/or adhesives, or screws may even totally be dispensed. Studies of cell vitality showed a good biocompatibility of the crosslinking product.

Accordingly, the invention comprises, in particular, also the use of the inventive kit, either having the two individual components "bridge molecules" and "polyphenoloxidases" or especially preferred having the three individual components "polymers having at least one free amino group," "bridge molecules," and "polyphenoloxidases" as defined above, for the manufacture of the inventive adhesive for the closure of wounds. By wounds, interruptions of the continuity of outer and inner body surfaces, such as e.g. incision wounds or fractures are meant. Accordingly, the invention, in particular, also comprises the use of the inventive kit for the manufacture of the adhesive for adhering of soft and hard tissue as well as adhering of bones with implants (e.g. a plate), as described above.

A very strong adhesion is formed in various fields of application, which, however, can be resorbed during the course of the healing process, by the crosslinking by means of the inventive combination, in particular by the bonding of peptide sequences containing the amino acids relevant for the adhesive action using the enzyme systems (lignolytic) polyphenoloxidase,-such as laccase. The initial healing phase in connection with good adhesive properties and the time-dependent slow resorption into the body during advanced healing processes are of special advantage.

The adhesive or the kit can be used in bone fracture for fixing vessel prostheses, biodegradable implants, catheters, stents, and other materials.

Accordingly, the invention comprises the use of the inventive kits, either with the two individual components "bridge molecules" and "polyphenoloxidases" or especially preferred with the three individual components "polymers having at least one free amino group," "bridge molecules," and "polyphenoloxidases" as defined above for the manufacture of an adhesive for adhering bone fractures and/or for fixing vessel prostheses, biodegradable implants, catheters, stents, and other materials.

Compatibility of implanted material with the bone cells is of fundamental importance for the adhering of bones as well as for the rapid integration of implants, in particular where bones are concerned. This, of course, also refers to the used adhesive. Due to the rapid growth of osteoblasts and their subsequent ripening, the formation of new bone is promoted and the healing process is shortened. Therefore, implants are provided with microstructured surfaces. The inventive kit or adhesive maintains this structure and supports the formation of new bone. The amino acids lysine and proline are required for the production of collagen, which is necessary for the healing of bones.

Preferably, (lysine-thyrosine)$_n$ is used as a polymer for this field of application. When using (lysine-thyrosine)$_n$ as a polymer, lysine is present at the adhesion site in high concentration. This results in a positive influence on the formation of bones. The formed extracellular matrix is identified using integrines, such as α1β1 or α3β1 because of the RDG sequence (Arg-Gly-Asp). This induces a signal cascade that causes changes in the cytoskeleton in the cell and switches between the stages of proliferation and differentiation. The formed protein matrix further serves the incorporation of calcium salts.

This enables the application in complicated fractures and the incorporation of bone fragments. The advantages of. the inventive combination of stopping of bleeding and high adhesive force are of great importance especially in the surgery of complicated fractures.

In a further aspect, the invention relates to novel zeolite granulates suitable for the stopping of bleeding that can be applied individually as well as used in addition to the inventive kit.

In particular, a rapid adhesion of the edges of wounds is achieved by the novel zeolite granulates.

The novel zeolite granulates are zeolite granulates having at least 70% by weight of zeolite, in particular having a proportion of clinoptilolite, chabasite, and mordenite, and a micropore volume having a medium pore size of 0.3-0.8 nm. Preferably, these zeolite granulates are free of hydrate, wherein this condition is preferably achieved after drying and precrushing by mild dehydration at temperatures below 200° C. In the mild dehydration, various temperature intervals below 200° C. are, in particular, used. Especially preferably, zeolite granulates are used that originate from the fraction having a corn band of 0.8-0.2 mm.

Regarding the purity of these zeolite granulates, all requirements according to US Pharmacorp. or Europ. Pharmacorp. are to be satisfied.

It has been found that certain factors involved in blood coagulation are selectively enriched in the micropore volume of these zeolite granulates. This leads to an activation of the physiological blood coagulation that causes the stopping of bleeding which is significantly superior over conventional haemostasis. In this connection, it is of special advantage that no toxic compounds are released to the wound. In the described inventive preparation, a zeolite granulate having strong electrostatic fields in the crystal lattice is obtained that can even stop strong bleeding within 1 min. Surprisingly, it has been found that the inventive zeolite granulates have a capillary force action that is fives to ten times superior over products on the basis of microporous synthetic lithium silicates (EP 1 176 991 A1, WO 00/69480, U.S. Pat. No. 6,833, 486 B1), e.g. CERDAC, available on the market. Due to the partial dehydration, no exothermal reaction occurs that may cause tissue damage by burning.

By means of the described inventive preparation, natural zeolites can now be provided for the first time in a cost-effective, direct way as means for stopping bleeding and means for the treatment of wounds. Accordingly, the present invention also comprises the inventive zeolite granulates as a medical product or as a medicament and the use of the inventive zeolite granulates for the manufacture of a medical product and/or a medicament for stopping of bleeding. As in the case of the kit, the classification as a pharmaceutical preparation or as a medical product, depending on national law, is possible. These terms are used in the context of the description of the invention synonymously.

As already mentioned above, it has been found that by means of the inventive zeolite granulates not only stopping of bleeding is achieved, but also a rapid adhesion of the wound edges. After the adhesion of the wound edges, the mineral material may be completely removed, for example, by detaching the scab-like wound coverage and extracting the remains. In this embodiment of the invention, it is possible to apply the zeolites in a covering, e.g. on the basis of cellulose or on a textile basis or on the basis of a collagen non-woven material. Thus, the subsequent complete removal is possible without any problems.

The wound edges are adhered to each other by activating the fibrin system. Accordingly, the invention also comprises the use of the inventive zeolite granulate for the manufacture of the inventive adhesive for adhering wounds as well as for sealing anastomases and patches to vessels or hollow organs, respectively.

The tear resistance of the wound closure is, however, lower than in conventional fibrin adhesives.

In order to increase the tear resistance, it is useful to use the inventive zeolite granulates in the above-described kit or adhesive. By this combination, especially effective haemostatic wound adhesives can be prepared for treatment of wounds, sealing of wounds, and stopping of bleeding. Accordingly, the present invention relates in a further embodiment to a kit, comprising the following individual components:

(a) Polymers having at least one free amino group,
(b) Bridge molecules, selected from the group consisting of monocyclic ortho-dihydroxyaromates, monocyclic para-dihydroxyaromates, bicyclic monohydroxyaromates, polycyclic monohydroxyaromates, bicyclic dihydroxyaromates, polycyclic dihydroxyaromates, bicyclic trihydroxyaromates, polycyclic trihydroxyaromates, and mixtures thereof,
(c) Polyphenoloxidases, in particular lignolytic polyphenoloxidases, and
(d) Minerals for stopping bleeding, in particular zeolite granulates as described above,
wherein both individual components (b), (c), and (d), i.e. the bridge molecules with the lignolytic polyphenoloxidases and the minerals for stopping bleeding, are not in contact.

Regarding the individual components and their preferred embodiments, it is referred to the description above. Accordingly, the kit is based, in particular, on natural zeolite fine granulates and on polyphenoloxidases in particular, laccase) by which the poly or oligopeptides, respectively, can be crosslinked.

Here it is preferred that the natural zeolite fine granulates are not in contact with the other individual components of the kit, i.e. it is preferred that the zeolite is packed separately and is used separately. Because of the high capillary force, the natural zeolite fine granulates cause a rapid closure of the wound by concentration of coagulation factors. Subsequently, the zeolites may be removed without a problem. A clear surgical area free of blood is maintained. It is further advantageous that possibilities for corrections, e.g. before adding the non-crosslinked polymers, if desired, are still given.

When the individual components (a) to (c) of the kit are initially provisionally applied to the closed wound, a wound closure is formed under development of covalent bonds that is, on the one hand, durable and loadable, but, on the other hand, also resorbable.

Of course, other means for stopping bleeding than the inventive zeolite granulates that make it possible to strongly reduce the loss of blood and, thus, removal of the (lignolytic) polyphenoloxidases, in particular laccase, at the application site may be considered. It is also possible after stopping bleeding using the natural zeolite fine granulates to use other tissue adhesives. However, the procedure described above—firstly stopping bleeding and closing the wound using natural zeolite fine granulates and subsequently durable adhesion involving the polyphenoloxidase, such as laccase—shows advantages and is superior over competing methods also under the viewpoint of costs. The inventive haemostatic kit for the treatment of wounds, sealing of wounds, as well as for adhering hard and soft tissue and implants is, furthermore, significantly easier to handle. The haemostatic adhesives can advantageously be used in plastic, reconstructive, and/or cosmetic surgery, in particular for avoiding the formation of scars induced during suturing of wounds, closure and sealing of liquid and air leakages, e.g. sealing of stitch channel bleedings in vessel surgery, in arterial bypass surgery, or for the sealing of lung leakages in thoracic surgery.

The inventive kit is an alternative to electrocoagulation as well as to closing of wounds using needle and thread.

Accordingly, the present invention also comprises the use of the inventive kit, comprising the individual components (b) to (d) or, more preferably, (a) to (d) for the manufacture of an adhesive for the closure of wounds. Furthermore, the invention in particular also comprises the use of the inventive kit, comprising the individual components (b) to (d) or, more preferably, (a) to (d) for the manufacture of an adhesive for adhering hard and soft tissue as well as adhering bones with implants (e.g. a plate) as described above.

Furthermore, the present invention also relates to an adhesive comprising components (b) to (d) or, more preferably, (a) to (d), as described as above, wherein the components (b) to (c) or (a) to (c), respectively, preferably all individual components (b) to (d) or (a) to (d), respectively, are in contact.

The high capillary force of the natural zeolite fine granulates is also of special importance for use in the treatment of wounds, in particular for the treatment of difficult-to-heal wounds and chronic wounds. Especially applicable is the use of the natural zeolite fine granulates in wounds having an exsudation, i.e. leaking of blood components from an infected wound. Exsudation is often an indication of an infection in an injury. The microporous structure of the zeolite granulates obtained according to the invention enables the absorption of wound exsudate that is released in "wetting" wounds in excess. Simultaneously, the absorption of excess exsudates provides a wet atmosphere over the wound, which is of importance for wound healing.

Further inventive uses are:

as a means for first aid after accidents for sanitation of infected wounds.

Completely surprisingly, it was found that zeolites having a pore width of 0.3-0.5 nm can be mixed with a biomass from aquatic organisms, as defined further below, in particular in a ratio of 1:10 to 10:1 without loss of the stopping effect on the bleeding or of capillary force.

Accordingly, the use of the novel zeolite granulates can be extended in that these materials are complemented with biomass. Accordingly, the present invention also comprises the inventive zeolite granulates, which additionally contain biomass, in particular in a ratio of zeolite to biomass of 1:10 to 10:1. Preferably selected according to the invention are microalgae having antibacterial activity, the biomass thereof is lyophilized and milled and/or processed according to the technical teaching of Lukowski et al.: Pharmaceutically or cosmetically active agent obtained from lipid-containing marine organisms, U.S. Ser. No. 10/507,061.

By mixing the natural zeolite fine granulates with biomass containing antimicrobial agents and being processed in that manner, it is possible to provide a combination that ensures the absorption of excess wound exsudate, keeps the wound wet, prevents infection of the wound, is non-inflammatory and immunostimulating, and promotes cell proliferation. Preferably selected in the preparation according to U.S. Ser. No. 10/507,061 are microalgae having a lipid content of >20% having lots of unsaturated fatty acids and/or having a high content of poly-N-acetyl-glucosamine. Thus, the antibacterial activity of the fatty acids can advantageously be used for this object.

Polysaccharides, advantageously from poly-N-acetyl-glucosamines or chitosane have a great inner surface. Due to the absorption onto this great surface, a synergistic effect regarding the concentration of coagulation factors as well as the absorption of wound secretion and bacterial toxins results. Furthermore, these polysaccharides have immunostimulating action. According to a preferred embodiment of the invention, lyophilized biomass of the green algae chlamydomonas and/or the microalgae spirulina and/or anabaena are used. By using the zeolites with or without biomass on a bleeding wound, a scab-like covering is formed by activating the fibrin system, which reliably protects the wound from bacterial infection. This covering is repelled in the course of wound healing.

In a suitable embodiment, the fine granulates from natural zeolites and microalgae biomass can also be used for treating highly infected, wetting wounds.

In various fields of application, the kit and/or adhesive can contain the inventive combination of zeolite granulate and biomass in all embodiments described in detail above.

The features of the invention can be taken not only from the claims, but also from the description, wherein the individual features on their own or in the form of combinations of more than one feature, respectively, are advantageous, patentable embodiments for which patent protection is requested in this application. The steps according to the invention can be used individually.

The invention will be described in more detail according to working examples without being limited to these examples.

EXAMPLES

Example 1

Preparation of the Natural Zeolite Fine Granulates

Selectively decomposed minerals having ≧70% zeolite content, preferably clinoptilolite, chabasite, and mordenite, are obtained after drying and precrushing with a corn band of 0.8 to 0.2 mm. With respect to purity, the requirements according to US Pharmacorp, or Europ, Pharmacorp, are to be satisfied. A partial dehydration while maintaining the crystal lattice structure is obtained by the mild thermal treatment in selected temperature intervals at temperatures<200° C.

Example 2

Testing the Micropore Volume and the Grain Size Distribution

The products obtained according to Example 1 exhibit 25-50% micropore volume (relative to the total volume) and a medium nanopore diameter in the range of 0.3-0.5 nm.

The nanopore size and the structure of the fine granulates enable a maximized blood absorption and a rapid penetration of the fine granulate resorbent.

The capillary force action is by five to ten times higher than in the commercial product CERDAC tested for comparative purposes.

Example 3

Testing the Fine Granulates for their Suitability for Stopping Bleeding

Method:
Two fine granulates, obtained according to Example 1, are tested.

The tests were carried out using rat liver as a prototype for an organ strongly supplied with blood. For this reason, rats were narcotized. After opening the abdominal area, a long cut of about 1 cm in length was made with a scalpel. The bleeding was filmed. The time period until stopping of the bleeding was measured.
Result:
The application of the inventive granulates leads to the stopping of the bleeding within 1 min. (control without treatment up to 8 min.). A scab-like covering is formed protecting the wound.

Example 4

In-Vitro Testing of the Fine Granulates for their Suitability for Stopping of Bleeding The following results were obtained in tests using various blood plasma:

| a) Normal plasma (with pre-incubation of 2 min.) | | | |
| --- | --- | --- | --- |
| | Normal plasma | Granulate 1 | Granulate 2 |
| Recalcification time | 115 s | 60 s | 60 s |
| PTT after 3-min. incubation | — | 15 s | Immediate clot |

Clot = Coagulation

| b) Deficient Plasma | | |
| --- | --- | --- |
| | Granulate 1 | Granulate 2 |
| F - VII MPI | Clot after 5 min. | Clot after 210 s |

There was no coagulation without granulate.

| c) Heparine plasma (with 2 and 3 min. preincubation) | | | | |
| --- | --- | --- | --- | --- |
| | Without | Granulate 1 | | Granulate 2 | |
| | granulate | 2 min. | 3 min. | 2 min. | 3 min. |
| 1. | 68 s | 46 s | 43 s | 65 s | 28 s |
| 2. | 45 s | 38 s | 17 s | 37 s | 10 s |

The results show that the endogenous coagulation system is activated, wherein the deficiency factor F-VII and tissue factor lead to increased trombine and fibrin formation. A relative increase of the fibrin concentration due to the mineral wound coverage according to Example 1 is also obtained.

Example 5

Testing of Extracts from Microalgae in View of their Antibacterial Efficiency

Method:
Various *staphylococcus* strains were uniformly distributed by means of a Whitley Automatic Spiral Plater on the agar-plate (Müller-Hinton-II-Agar ready-to-use plates by Becton Dickinson).

An amount of extract solution corresponding to 2 mg extract is dropped onto acetate tissue as used for the manufacture of a wound coverage and is allowed to dry.

Lyophilized biomasses of the green algae *chlamydomonas*, of the microalgae *spirulina* (Blue Biotech Büsum) and *Anabaena* (strain collection by the Department of Pharmacy at the Ernst-Moritz-Arndt University of Greifswald) were used for the manufacture of the extracts. The extractor DIONEX ASE 200 was used for the extraction with n-hexane. The extract solution was separated from the solvent using a rotary evaporator.
Result:
Seventy to one hundred twenty seeds/cm$^2$ were counted in the control. No germs of *staphylococcus aureus* strains resistant to methicillin (MRSA) that may cause wound infections were found beneath the wound coverage. Other *straphylococca* showed a reduced germ growth of 10% to 20% of the initial germ number.

Example 6

Manufacture of Fine Granulates from Natural Zeolites and the Biomass of Microalgae Microalgae biomasses having a lipid content of >20% can be admixed to the mineral fine granulates obtained according to Example 1 in a ratio of 1:10 to 10:1. Thus, infection of wounds can be prevented.

Example 7

Testing of the Fine Granulates for Their Suitability for Stopping Bleeding and for Wound Closure a) Method:

Two fine granulates, obtained according to Example 1, were tested.

The tests were carried out using rat liver as a prototype for an organ strongly supplied with blood. For this reason, the rats were narcotized. A long cut of about 1 cm in length was made with a scalpel after opening of the abdominal area. The bleeding was filmed. The time period until stopping of the bleeding was measured. The wound closure was rated visually.

Result:

The application of the inventive granulate leads to a stopping of the bleeding within 1 min. (control up to 8 min.). A scab-like covering is formed protecting the wound.

b) The covering was removed with a scalpel after 1 min. in further tests.

Result:

A wound having a superficially closed surface that is no longer bleeding and having a visually rated good wound closure is obtained. The wound closure in case of fine granulates on mineral material/algae biomass basis is superior over the use of preparations that are exclusively prepared on a mineral basis.

c) The fine granulates were separated from the wound in further tests using a cellulose patch.

Result:

Under these conditions, stopping of bleeding within less than 1 min. Is obtained. A clear surgical area is obtained so that a strong adhesion of the wound using the tissue adhesive according to the invention can be carried out without any problem.

Example 8

Manufacture of the Adhesive Prepolymers and Carrying Out of the Adhesive Reaction for Adhesion of Hard and Soft Tissue The developed adhesive results in mixture of the individual components oligopeptide 1 (amino acid sequence consisting of dipeptide repeating units of tyrosine and lysine, n=5 or n=10), bridge molecule 2 (2,5-dihydroxy-N-(2-hydroxyethyl)-benzamide) and the enzyme laccase (Scheme 5). The tests were carried out in phosphate buffer.

Scheme 5:

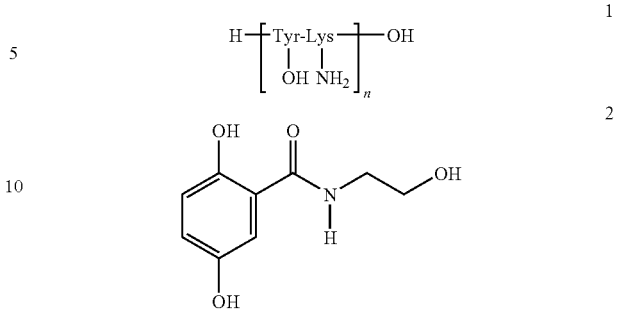

The adhesive action is based on the enzymatic reaction of the laccase with the bridge molecule that is being connected with the oligopeptide.

The following mixing ratios were employed:

$[Tyr-Lys]_n$, $n=4-35$, 8.5 mM; 2,5-dihydroxy-N-(2-hydroxyethyl)-benzamide 12.5 mM; enzyme: 0.32 U (156 nmol ml$^{-1}$ min$^{-1}$). The solvent content of methanol was 10% (v/v).

Example 9

Testing of the Firmness of the Adhesion Seam

For testing the firmness of the adhesion seam in the pulling test, the tissue parts to be tested had to be fixed in advance. Porcine soft tissue was fixed with cyanacrylate adhesive on sample carriers made of polymethyl methacrylate (PMMA) or bone plates of bone of bovine origin were clamped in mechanical clamps. Subsequently, the adhesive mixture to be tested (cf: Example 6) was applied to the tissue. When adhering soft tissue, the firmness of the adhesion seam was determined after 10 minutes under pulling stress in the measuring apparatus Zwick BZ2.5/TN1S (scan rate: 10 mm/min). The mechanical testing of the adhesion seam when adhering hard tissue was carried out using pulling shear stress with a scan rate of 5 mm/min.

Result: Two times the firmness is obtained in comparison to the tested commercially available fibrin adhesives.

Example 10

Diffusion Inhibition Test Using a Collagen Non-Woven Material Treated According to the Invention in Comparison to a Non-Woven Material Treated with a Conventional Antibiotic Method:

The agar diffusion test according to Burkhardt (Burkhardt, F. (Hrsg.) Mikrobiologische Diagnostik. Georg-Thieme Verlag Stuttgart, N.Y. 1992, p. 724) was carried out. Mueller-Hinton II-Agar in Stacker Petri dishes (Becton Dickinson Microbiology Systems, Cockeysville, USA) were employed in the test for 15. The strain *S. aureus* ATCC 6538 was selected as test strain. The initial seed of this test strain was chosen such that after 1620 hours of incubation, closely standing, but not confluent, single colonies had developed. After drying of the seeded culture media, the treated collagen non-woven material was applied to the agar surface. After 18+2 hours incubation at 36° C., the inhibition sphere was measured.

Results:

| | Inhibition sphere against S. aureus ATCC 6538 | |
|---|---|---|
| Treatment | Gentamycine | Non-woven material treated acc. to the invention |
| 15% | | 30 |
| 20% | 24 | 36 |
| 30% | | 38 |
| 40% | 38 | |

The non-woven material according to the invention has the following advantages:
  Improved antimicrobial activity, also against multi-resistant germs
  Very good haemostatic action
  Good adhesion on the wound and easy application Example 11

Testing of Surfaces Treated with Polyphenols According to the Invention Regarding Antibacterial Efficiency Method:

Various *staphylococcus* strains were uniformly distributed on the agar plate (Mueller-Hinton-II-Agar ready-to-use plates of Becton Dickinson) by means of a Whitley Automatic Spiral Plater in linear modus.

Polymer biomaterials (1 cm² each) were functionalized according to Contrib. Plasma Phys. 41, 2001, 562-572 in ammonik plasma. Subsequently, reaction with 2,5-dihydroxy-N-(2-hydroxyethyl)-benzamide (12.5 mM) under the influence of the laccase (0.32 U (156 nmol ml$^{-1}$ min$^{-1}$) was carried out. The solvent content of methanol was 10% (v/v).

After drying, the plates were put onto the agar.

Result:

One hundred twenty germs/cm² were counted in the control. Under the coated surfaces no germs could be detected.

Example 12

Use of the Combination According to the Invention for Treating Bleeding Wounds

Method:

Rats were narcotized as in Example 7, the abdominal area was opened and a cut was made into the liver. The bleeding was stopped as in Example 7c, the crust in formation was removed. Subsequently, the cut was fixed with wound adhesive.

For this purpose, the oligopeptides described in Example 6 were incorporated in PBS (phosphate buffered saline, 2.7 M NaCl, 54 mM KCl, 87 mM Na$_2$HPO$_4$, 30 mM KH$_2$PO$_4$, pH 7.4) and laccase was added (component 1). 2,5-dihydroxy-N-(2-hydroxyethyl)-benzamide was dissolved in PBS (component 2). Different ratios of oligopeptide/2,5-dihydroxy-N-(2-hydroxyethyl)-benzamide/laccase were tested, e.g. 1/1/0, 1; 1/2/0,5; 1/10/1). A minimum amount of solvent was selected in order to have a solution of the components of maximum concentration. The components were put into a two-compartment syringe having a mixing extruder of the type Mixpac (Mixpac Systems, Rotkreuz, Switzerland) and were applied to the wound fissure.

Result: A good wound closure was achieved with haemostatics. The adhesive can be put directly into the resulting narrow fissure. The result is a very strong adhesion of the wound edges.

Example 13

Adhering of Collagen

Method:

Collagen foil (DOT GmbH) was fixed on a flat carrier.

The collagen foil was divided into 8 segments (or in two rows) and the adhesive was mixed directly on the foil (by using the surface tension). The adhesive was dissolved in phosphate citrate buffer.

Different concentrations of bridge molecules (laccase substrate) were tested. The adhesive protein had an MW of about 4,000 D.

Subsequently, small pieces of collagen foil were applied, pressed softly and were allowed to dry.

Result:

When adhering collagen, a strong bond was achieved.

Adhesion also results without the addition of adhesive proteins. However, the adhesive force was increased by the adhesive proteins.

Example 14

Mixing of a Collagen Solution with the Adhesive

A significant structuring can be detected under the microscope when mixing the collagen solution with the adhesive. The dissolved and incidentally ordered collagen molecules were made parallel while forming fibers.

Example 15

Adhering Collagen and Polystyrene

Method:

A drop of citrate phosphate buffer (20 µl, control) or adhesive solution (buffer, laccase, laccase substrate) were applied onto the surface of a 60 mm TCPS cell culture vessel and a small piece of collagen foil (8×4 mm) was applied, respectively, pressed smoothly and was then allowed to dry.

Result:

Despite the smooth and inert surface, an adhesion was achieved. The collagen was durably bonded to the carrier.

Example 16

Cell Adhesion onto the Surfaces Loaded with Collagen

Method:

Cell adhesion was tested using a fibroblast cell line (FL cells).

Cell adhesion occurred on a 60 mm TCPS cell culture vessel that was coated with collagen as in Example 15. After coloring the cells with crystal violet, evaluation was done with the CellExplorer.

Result:

The FL cells were bonded more strongly.

The invention claimed is:
1. A kit comprising the following individual components:
(a) polymers having at least one free amino group;
(b) bridge molecules, selected from the group consisting of monocyclic ortho-dihydroxyaromates, monocyclic para-dihydroxyaromates, bicyclic monohydroxyaromates, polycyclic monohydroxyaromates, bicyclic dihydroxyaromates, polycyclic dihydroxyaromates, bicyclic trihydroxyaromates, polycyclic trihydroxyaromates, and mixtures thereof; and
(c) polyphenoloxidases,
wherein the individual components (b) and (c) are not in contact.
2. The kit according to claim 1, wherein the free amino group is obtained through a diamino acid.
3. The kit according to claim 1, or claim 2, wherein the polymers are in contact with the dihydroxyaromates.
4. The kit according to any one of claim 1 or 2, wherein the kit is a syringe having two cannulae by which the dihydroxyaromates and the polyphenoloxidases can be administered separately.
5. An adhesive comprising the following components:
(a) polymers having at least one free amino group, wherein the polymers are not part of the human body;
(b) bridge molecules, selected from the group consisting of monocyclic ortho-dihydroxyaromates, monocyclic para-dihydroxyaromates, bicyclic monohydroxyaromates, polycyclic monohydroxyaromates, bicyclic dihydroxyaromates, polycyclic dihydroxyaromates, bicyclic trihydroxyaromates, polycyclic trihydroxyaromates, and mixtures thereof; and
(c) polyphenoloxidases,
wherein the individual components (b) and (c) are in contact.
6. The adhesive according to claim 5, wherein the individual components (a)-(c) are in contact.
7. The kit of claim 1 or adhesive of claim 5, wherein the kit or adhesive comprises as a further individual component (d) a zeolite granulate.
8. The kit according to claim 7, wherein the zeolite granulate is not in contact with the other individual components (a) to (c).
9. The adhesive according to claim 7, wherein the zeolite granulate is in contact with the other individual components.
10. The kit of claim 1 or adhesive of claim 5, wherein the aromates (b) are substituted.
11. The kit of claim 1 or adhesive of claim 5, wherein the dihydroxyaromates are 2,5-dihydroxybenzamides.
12. The kit of claim 1 or adhesive of claim 5, wherein the dihydroxyaromates are 2,5-dihydroxy-N-(2-hydroxyethyl)-benzamide.
13. The kit of claim 1 or adhesive of claim 5, wherein the polyphenoloxidases are laccases.
14. The kit of claim 1 or adhesive of claim 5, wherein the polymers are selected from the group consisting of oligopeptides, peptides, and proteins.
15. The kit of claim 1 or adhesive of claim 5, wherein the polymers contain lysine.
16. The kit of claim 1 or adhesive of claim 5, wherein the polymers are lysine-containing oligopeptides or collagen.
17. The kit as set forth in claim 1 wherein the polyphenoloxidases are lignolytic polyphenoloxidases.
18. A method for forming a surgical adhesive comprising providing a polymer component having at least one free amino group and crosslinking the polymer component by means of bridge molecules using a polyphenoloxidase component, wherein the bridge molecules are selected from the group consisting of monocyclic ortho-dihydroxyaromates, monocyclic para-dihydroxyaromates, bicyclic monohydroxyaromates, polycyclic monohydroxyaromates, bicyclic dihydroxyaromates, polycyclic dihydroxyaromates, bicyclic trihydroxyaromates, polycyclic trihydroxyaromates, and mixtures thereof.
19. The method as set forth in claim 18 further comprising:
the polymer component having at least one free amino group, the polyphenoloxidases component and the component containing bridge molecules are contained in two separate storage chambers prior to crosslinking, with the polyphenoloxidases and the bridge chambers molecules supplied in separate chambers of the two chambers.
20. The method as set forth in claim 19, wherein the separate chambers are two separate syringes.
21. The method as set forth in claim 19 further comprising mixing zeolite granules into at least one of the two chambers containing the components.
22. The method as set forth in claim 19, wherein the polymer having at least one free amino group is a peptide.
23. The method as set forth in claim 22, wherein the peptide comprises at least one diamino acid.
24. The method as set forth in claim 19, wherein the components are dissolved in a phosphate buffer.
25. A method for closing a wound comprising:
providing a polymer component having at least one free amino group and crosslinking the polymer component by means of bridge molecules using a polyphenoloxidase component wherein the bridge molecules are selected from the group consisting of monocyclic ortho-dihydroxyaromates, monocyclic para-dihydroxyaromates, bicyclic monohydroxyaromates, polycyclic monohydroxyaromates, bicyclic dihydroxyaromates, polycyclic dihydroxyaromates, bicyclic trihydroxyaromates, polycyclic trihydroxyaromates, and mixtures thereof, the polyphenoloxidase component and the bridge molecules contained in separate chambers;
discharging the components from each chamber and forming a mixture; and
applying the mixture to the wound.
26. A kit comprising the following individual components:
(a) polymers having at least one free amino group;
(b) bridge molecules, selected from the group consisting of monocyclic ortho-dihydroxyaromates, monocyclic para-dihydroxyaromates, bicyclic dihydroxyaromates, polycyclic dihydroxyaromates, bicyclic trihydroxyaromates, polycyclic trihydroxyaromates, and mixtures thereof; and
(c) polyphenoloxidases,
wherein the individual components (b) and (c) are not in contact.
27. An adhesive comprising the following components:
(a) polymers having at least one free amino group, wherein the polymers are not part of the human body;
(b) bridge molecules, selected from the group consisting of monocyclic ortho-dihydroxyaromates, monocyclic para-dihydroxyaromates, bicyclic dihydroxyaromates, polycyclic dihydroxyaromates, bicyclic trihydroxyaromates, polycyclic trihydroxyaromates, and mixtures thereof; and
(c) polyphenoloxidases,
wherein the individual components (b) and (c) are in contact.

* * * * *

UNITED STATES PATENT AND TRADEMARK OFFICE
CERTIFICATE OF CORRECTION

| | | |
|---|---|---|
| PATENT NO. | : 7,923,003 B2 | Page 1 of 1 |
| APPLICATION NO. | : 12/223772 | |
| DATED | : April 12, 2011 | |
| INVENTOR(S) | : Andreas Speitling et al. | |

It is certified that error appears in the above-identified patent and that said Letters Patent is hereby corrected as shown below:

On the cover page, item [75] inventor: "Wolf Dieter Jüllch" should read --Wolf-Dieter Jüllch--.
Column 21, line 50, "1 min. Is" should read --1 min. is--.
Column 25, line 18, "one of claim" should read --one of claims--.

Signed and Sealed this
First Day of January, 2013

David J. Kappos
*Director of the United States Patent and Trademark Office*

UNITED STATES PATENT AND TRADEMARK OFFICE
CERTIFICATE OF CORRECTION

PATENT NO.         : 7,923,003 B2                                                Page 1 of 1
APPLICATION NO.    : 12/223772
DATED              : April 12, 2011
INVENTOR(S)        : Andreas Speitling et al.

It is certified that error appears in the above-identified patent and that said Letters Patent is hereby corrected as shown below:

On the Title page, item [75] inventor: "Wolf Dieter Jüllch" should read --Wolf-Dieter Jūlich--.

In the Specifications
Column 21, line 50, "1 min. Is" should read --1 min. is--.

In the Claims
Column 25, line 18, "one of claim" should read --one of claims--.

This certificate supersedes the Certificate of Correction issued January 1, 2013.

Signed and Sealed this
Fourth Day of February, 2014

Michelle K. Lee
*Deputy Director of the United States Patent and Trademark Office*